United States Patent [19]

Matsumoto et al.

[11] Patent Number: 4,460,596

[45] Date of Patent: Jul. 17, 1984

[54] THIENYLOXAZOLYLACETIC ACID DERIVATIVES AND PROCESS FOR PREPARING

[75] Inventors: Kazuo Matsumoto, Ibaraki; Kohki Takashima, Tokyo, both of Japan

[73] Assignee: Tanabe Seiyaku Co., Ltd., Osaka, Japan

[21] Appl. No.: 372,990

[22] Filed: Apr. 29, 1982

[30] Foreign Application Priority Data

May 15, 1981 [JP] Japan .................. 56/73777

[51] Int. Cl.³ .................. C07D 263/32; A61K 31/42
[52] U.S. Cl. .................. 424/272; 548/235; 548/237
[58] Field of Search .................. 548/235, 237; 424/272

[56] References Cited

U.S. PATENT DOCUMENTS 3,574,228  4/1971  Brown et al. .................. 548/235
3,579,529  5/1971  Brown et al. .................. 548/235
4,012,412  3/1977  Yamanaka et al. .................. 548/235

OTHER PUBLICATIONS

Yamanaka et al., Chemical Abstracts, 88:89653c, (1978).

Primary Examiner—Donald G. Daus
Assistant Examiner—S. A. Gibson
Attorney, Agent, or Firm—Jordan B. Bierman; Linda Bierman

[57] ABSTRACT

A compound of the formula

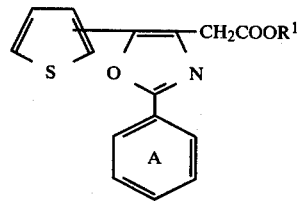

wherein Ring A is phenyl or halogenophenyl and $R^1$ is hydrogen or lower alkyl, or a pharmaceutically acceptable salt thereof and processes for preparing the same are disclosed. Said compound is useful as a hypolipidemic agent.

17 Claims, No Drawings

THIENYLOXAZOLYLACETIC ACID DERIVATIVES AND PROCESS FOR PREPARING

This invention relates to novel thienyloxazolylacetic acid derivatives and processes for preparing same. More particularly, it relates to thienyloxazolylacetic acid derivatives of the formula:

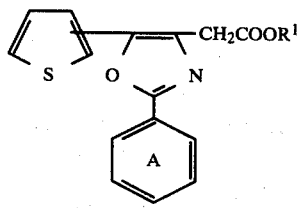

wherein Ring A is phenyl or halogenophenyl and $R^1$ is hydrogen or lower alkyl, or a pharmaceutically acceptable salt thereof.

Hyperlipidemia is known to be one of important causative factors of arteriosclerosis, and various compounds such as dextran sulfate, simfibrate (chemical name: 2-(4-chlorophenoxy)-2-methylpropanoic acid 1,3-propanediyl ester), nicomol (chemical name: nicotinic acid 1,1,3,3-tetraester with 2-hydroxy-1,1,3,3-cyclohexanetetramethanol), clofibrate (chemical name: 2-(4-chlorophenoxy)-2-methylpropanoic acid ethyl ester) and vitamin E nicotinate have been used for the treatment or prophylaxis of said hyperlipidemia.

As a result of investigations, it has now been found that the thienyloxazolylacetic acid derivatives (I) of the present invention are useful as a hypolipidemic agent. In particular, the thienyloxazolylacetic acid derivatives (I) shows potent hypolipidemic activity without undesirable side effects such as hepatic disfunction. Further, the thienyloxazolylacetic acid derivatives (I) also show a potent platelet aggregation-inhibiting activity.

Representative examples of the thienyloxazolylacetic acid derivatives include those of the formula (I) in which thienyl group is 2-thienyl or 3-thienyl; Ring A is phenyl or halogenophenyl such as fluorophenyl, chlorophenyl, bromophenyl and iodophenyl; and $R^1$ is hydrogen or lower alkyl such as methyl, ethyl, n-propyl, isopropyl, n-butyl, isobutyl, n-pentyl and isopentyl. Among them, a preferred subgenus is the compound of the formula (I) in which Ring A is phenyl, 4-fluorophenyl, 2-chlorophenyl, 3-chlorophenyl or 4-chlorophenyl, and $R^1$ is hydrogen, methyl, ethyl, isopropyl, n-butyl or n-pentyl. Another preferred subgenus is the compound of the formula (I) in which Ring A is phenyl, 4-fluorophenyl or 4-chlorophenyl, and $R^1$ is hydrogen, ethyl, n-butyl or n-pentyl. More preferred subgenus is the compound of the formula (I) in which Ring A is phenyl, 4-fluorophenyl or 4-chlorophenyl, and $R^1$ is hydrogen, ethyl or n-pentyl. Further preferred subgenus is the compound of the formula (I) in which Ring A is phenyl or 4-fluorophenyl, and $R^1$ is ethyl or n-pentyl.

According to the present invention, the compound (I) in which $R^1$ is lower alkyl is prepared by subjecting a 3-benzoylaminopropionate derivative of the formula:

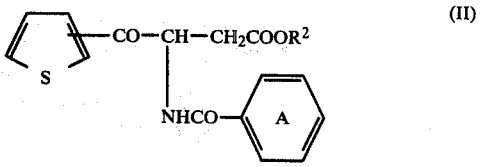

wherein $R^2$ is lower alkyl and Ring A is the same as defined above, to dehydrative cyclization to give a thienyloxazolylacetate derivative of the formula:

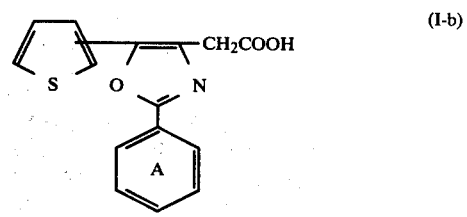

wherein Ring A and $R^2$ are the same as defined above.

Further, the compound (I) in which $R^1$ is hydrogen is prepared by hydrolyzing the compound (I-a) obtained above to give a thienyloxazolylacetic acid derivative of the formula:

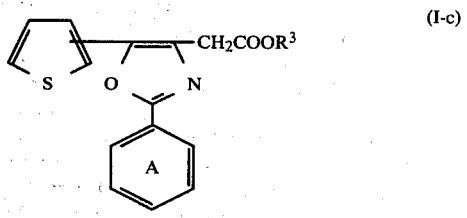

wherein Ring A is the same as defined above.

Furthermore, the compound (I) in which $R^1$ is lower alkyl may be prepared by subjecting the compound (I-b) obtained above to esterification to give a thienyloxazolylacetate derivative of the formula:

wherein $R^3$ is lower alkyl and Ring A is the same as defined above.

The dehydrative cyclization of the compound (II) is accomplished in a solvent in the presence of a dehydrating agent. Suitable examples of the dehydrating agent include phosphorus oxychloride, thionyl chloride, phosphorus pentachloride and phosphoric anhydride. Dimethylformamide, benzene, toluene, tetrahydrofuran, xylene and chloroform are suitable as the solvent. It is preferred to carry out the reaction at a temperature of $-5°$ to $100°$ C., especially $0°$ to $10°$ C.

The hydrolysis of the compound (I-a) is accomplished by contacting said compound with an acid or an alkali agent in a solvent. Suitable examples of the acid include mineral acids such as hydrochloric acid or sulfuric acid. On the other hand, suitable examples of the alkali agent include alkali metal hydroxides such as sodium hydroxide or potassium hydroxide. A mixture of water and alkanol (e.g., methanol, ethanol, propanol), tetrahydrofuran, dioxane, formic acid or acetic acid is suitable as the solvent. It is preferred to carry out the reaction at a temperature of 0° to 100° C., especially 10° to 30° C.

The esterification of the compound (I-b) is accomplished by reacting a reactive derivative of said compound with an alkanol of the formula: $R^3$—OH (wherein $R^3$ is the same as defined above). Suitable examples of the reactive derivative of the compound (I-b) include the corresponding acid halides (e.g., chloride, bromide) and mixed anhydride (e.g., ethoxycarbonyl ester, isobutyloxycarbonyl ester). Especially, it is preferred to use the acid halide as the reactive derivative of the compound (I-b). On the other hand, the alkanol ($R^3$—OH) include, for example, methanol, ethanol, n-propanol, isopropanol, n-butanol, isobutanol, n-pentanol and isopentanol. When the acid halide of the compound (I-b) is used, the esterification is conducted in a solvent in the presence or absence of an acid acceptor. Suitable examples of the acid acceptor include triethylamine, tributylamine, sodium carbonate and sodium bicarbonate. Methylene chloride, chloroform, ethyl acetate, tetrahydrofuran, benzene, dioxane and dimethylformamide are suitable as the solvent. When an excess of the alkanol ($R^3$—OH) is used, it is not always necessary to use the solvent because said alkanol serves as the solvent. It is preferred to carry out the reaction at a temperature of $-10°$ to 20° C. Concomitantly, the acid halide of the compound (I-b) which is used in the above-mentioned reaction is prepared by reacting the compound (I-b) or its alkali metal or alkali earth metal salt (e.g., sodium salt, potassium salt, magnesium salt, calcium salt) with a halogenating agent in a solvent. Suitable examples of the halogenating agent include thionyl chloride, oxazolyl, chloride, phosphorus pentachloride and phosphorus trichloride. Toluene, tetrahydrofuran, dioxane and chloroform are suitable as the solvent. When an excess of the halogenating agent is used, it is not always necessary to use the solvent because said halogenating agent serves as the solvent. It is preferred to carry out the halogenation reaction at a temperature of $-10°$ to 20° C.

Alternatively, the esterification of the compound (I-b) is conducted by reacting said compound with the alkanol ($R^3$—OH) in a solvent in the presence of a dehydrating agent. Suitable examples of the dehydrating agent include 2-chloro-1-methylpyridinium iodide, 2-bromo-1-methylpyridinium iodide and dicyclohexylcarbodiimide. Tetrahydrofuran, dioxane, toluene and chloroform are suitable as the solvent. It is preferred to carry out the reaction at a temperature of 0° to 30° C. When 2-chloro-1-methylpyridinium iodide or 2-bromo-1-methylpyridinium iodide is used as the dehydrating agent, it is also preferred to carry out the reaction in the presence of an acid acceptor (e.g., triethylamine, tributylamine, pyridine).

Further, the esterification of the compound (I-b) is conducted by reacting said compound with the alkanol ($R^3$—OH) in the presence of an acid. p-Toluenesulfonic acid, hydrochloric acid and sulfuric acid are suitable as the acid. It is preferred to carry out the reaction at a temperature of 50° to 100° C.

Furthermore, the esterification of the compound (I-b) is conducted by reacting said compound with an alkyl halide of the formula: $R^3$—X (wherein X is halogen and $R^3$ is the same as defined above) in a solvent. Suitable examples of the alkyl halide include methyl iodide, ethyl iodide, n-propyl bromide, n-propyl iodide, n-butyl bromide and n-pentyl chloride. Tetrahydrofuran, dioxane, chloroform, benzene, toluene and dimethylformamide are suitable as the solvent. It is preferred to carry out the reaction at a temperature of 50° to 100° C.

In view of the potent hypolipidemic activity of the compound (I) obtained above, said compound of the present invention is useful for the therapeutic treatment or prophylaxis of various hyperlipidemias such as hyperchlolesterolemia, hypertriglyceridemia, hyperlipemia and the like. Moreover, the compound (I) of the present invention shows less hepatomegaly or other hepatic disorders as compared with clofibrate, and is particularly suitable for treatment of the above-mentioned diseases without such undesirable side effects. Further, the compound (I) of the present invention has a potent platelet aggregation-inhibiting activity which is desirable for the hypolipidemic agent.

The compound (I) ($R^1$=H) of the present invention can be used for pharmaceutical use either in the free form or in the form of a salt thereof. Pharmaceutically acceptable salts of the compound (I) ($R^1$=H) include, for example, metallic salts such as sodium, potassium, calcium and magnesium salts; salts thereof with amino acids such as lysine, ornithine and arginine salts; and ammonium salt. The compound (I) and a salt thereof can be administered either orally or parenterally. For oral administration, the compound (I) or a salt thereof may be used in the form of tablets, powder, capsules, granules and the like. Known medicinal excipients such as calcium carbonate, calcium phosphate, corn starch, potato starch, sugar, lactose, talc, magnesium stearate and so forth may be used in making these pharmaceutical preparations. Alternatively, the compound (I) or a salt thereof may be used for oral administration in the form of aqueous or oily suspensions, solutions, syrups or elixirs. On the other hand, injections and suppositories are suitable for parenteral administration of the compound (I) or its salts, and said injections may be made in the form of solutions or suspensions, if required, in conjunction or admixture with distilled water, essential oil (e.g., peanut oil, corn oil) or non-aqueous solvents (e.g., polyethyleneglycol, polypropyleneglycol, lanoline, coconut oil). The daily dose of the compound (I) or a salt thereof may vary depending on the administration route, the age, weight or conditions of patients, and the severity of diseases to be treated. In general, however, a preferred daily dose of said compound (I) or a salt thereof may be 1 to 20 mg, especially 5 to 15 mg, per kilogram of body weight per day.

Concomitantly, the starting compound (II) of the present invention is a novel compound and can be prepared, for example, according to the method shown in the following reaction scheme:

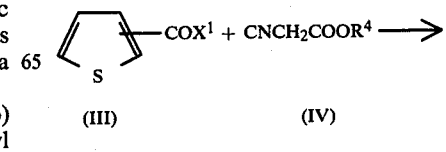

(III)                (IV)

-continued

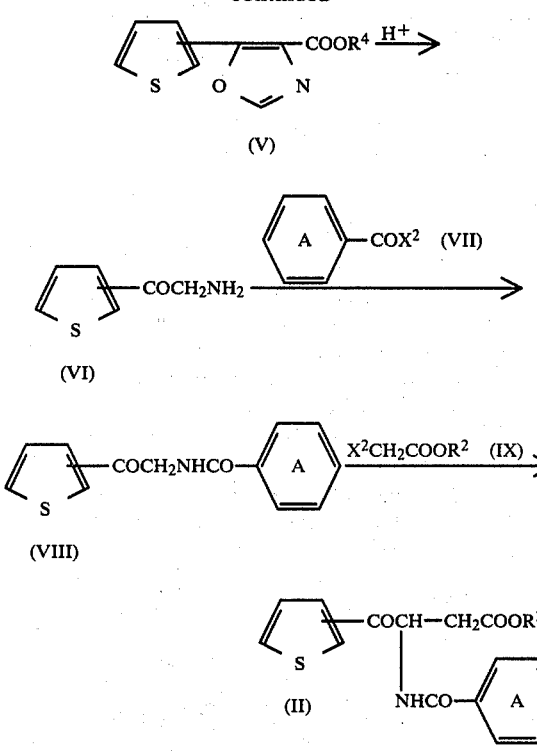

wherein $R^4$ is lower alkyl, $X^1$ is halogen or a group of the formula:

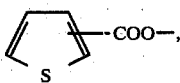

$X^2$ is halogen, and Ring A and $R^2$ are the same as defined above.

The reaction of the thiophenecarboxylic acid derivative (III) with the isocyanoacetate compound (IV) is carried out in a solvent (e.g., tetrahydrofuran, dioxane, benzene, toluene, dimethylformamide) in the presence of triethylamine, potassium t-butoxide or 1,8-diazabicyclo(5.4.0)undecene at −50° to 50° C. The oxazole derivative (V) thus obtained is then treated with a mineral acid (e.g., 3–6N hydrochloric acid) at 40° to 100° C. to give the aminoketone compound (VI). The subsequent reaction of the aminoketone compound (VI) with the benzoyl halide compound (VII) is carried out in a solvent (e.g., ethyl acetate, benzene) in the presence of an acid acceptor (e.g., sodium hydroxide, sodium bicarbonate) at −10° to 50° C. The benzoylamine compound (VIII) thus obtained is then reacted with halogenoacetate compound (IX) in a solvent (e.g., tetrahydrofuran, dioxane, benzene, toluene, dimethylformamide, dimethylsulfoxide) in the presence of an acid acceptor (e.g., sodium hydride, potassium t-butoxide, n-butyl lithium) at −50° to 30° C. to give the 3-benzoylaminopropionate compound (II).

Practical and presently-preferred embodiments of the present invention are illustratively shown in the following lines. Throughout the specification and claims, the term "lower alkyl" should be interpreted as referring to alkyl of one to five carbon atoms.

Experiment 1

(Hypolipidemic activity)

A test compound (50 mg %) was added to a commercial diet, and male SD rats (body weight: 120–140 g, a group of 5 rats) were fed with the diet ad libitum for one week. After the experimental period, blood was collected from the tail vein of the rats under ether anesthesia. Serum cholesterol and serum triglyceride were measured according to the methods of Zak (Amer. J. Clin. Pathol., Vol. 24, page 1307(1954)) and Van Handel-Zilversmit (J. Lab. & Clin. Med., Vol. 55, page 152(1957)), respectively. Then, the increase (%) in liver weight and the decrease (%) in serum cholesterol or triglyceride were calculated according to the following formulae:

Decrease (%) in serum cholesterol or triglyceride =

$$\left[ 1 - \frac{\text{Serum cholesterol or triglyceride (mg/ml) in the medicated group}}{\text{Serum cholesterol or triglyceride (mg/ml) in the control group}} \right] \times 100$$

Increase (%) in liver weight =

$$\left[ \frac{\text{Liver weight in the medicated group}}{\text{Liver weight in the control group}} - 1 \right] \times 100$$

(Results)

The results are shown in the following Table 1. Concomitantly, each of the test compounds of the present invention showed no substantial increase in liver weight, whereas clofibrate showed 12% increase in liver weight.

TABLE 1

| Test compound | Decrease (%) in serum cholesterol | Decrease (%) in serum triglyceride |
|---|---|---|
| (The compounds of the present invention) | | |
| Ethyl 2-[2-(4-fluorophenyl)-5-(3-thienyl)-4-oxazolyl]acetate | 19 | 31 |
| Ethyl 2-[2-(4-fluorophenyl)-5-(2-thienyl)-4-oxazolyl]acetate | 17 | 43 |
| 2-[2-(4-fluorophenyl)-5-(3-thienyl)-4-oxazolyl]acetic acid | 23 | 39 |
| 2-[2-(4-fluorophenyl)-5-(2-thienyl)-4-oxazolyl]acetic acid | 17 | 27 |
| 2-[2-(4-chlorophenyl)-5-(3-thienyl)-4-oxazolyl]acetic acid | 18 | 49 |
| n-Pentyl 2-[2-(4-chlorophenyl)-5-(3-thienyl)-4-oxazolyl]acetate | 19 | 45 |
| n-Pentyl 2-[2-phenyl-5-(3-thienyl)-4-oxazolyl]acetate | 20 | 30 |
| (Positive control) | | |
| Clofibrate | 15 | 16 |

Experiment 2

(Platelet aggregation-inhibiting activity)

Blood was collected from the abdominal aorta of male SD rats (body weight: 250–300 g) which were anesthetized with ether. Nine volumes of said blood were mixed with one volume of an aqueous 3.8% (w/v) trisodium citrate solution, and the mixture was centrifuged at 500×g for 5 minutes to give platelet-rich plasma (hereinafter referred to as "PRP") as the supernatant solution. The bottom layer was further centrifuged at 1000×g for 10 minutes to give platelet-poor plasma (hereinafter referred to as "PPP") as the supernatant solution. PRP was diluted with PPP so that the blood platelet count was $8-10\times10^5/mm^3$. Then, a mixture of 200 μl of said diluted PRP and 25 μl of a test compound solution (final concentration: 100 μg/ml) was introduced into a glass cell of SIENCO aggregometer (Sienco Inc., Morrison, Colo. Model DP-247-D). After the mixture was stirred at 1100 rpm at 37° C. for 2 minutes, 25 μl of a collagen solution (prepared by Holmsen's method described in Biochim. Biophys. Acta, Vol. 186, page 254(1969)) was added thereto, and the percentage inhibition of platelet aggregation was calculated in accordance with the following formula from the degree of the platelet aggregation which was estimated by Born's method (Nature, 194, page 927(1969)).

Percentage inhibition of platelet aggregation =

$$\left[1 - \frac{\text{Degree of platelet aggregation which was estimated by adding test compound}}{\text{Degree of platelet aggregation which was estimated without adding test compound}}\right] \times 100$$

Further, on the basis of said percentage inhibition calculated above, the platelet aggregation-inhibiting activity of the test compound was expressed as (−) if the test compound showed less than 10% inhibition of platelet aggregation; or (+) if the test compound showed not less than 10% inhibition of platelet aggregation.

(Results)
The results are shown in the following Table 2.

TABLE 2

| Test compounds | Platelet aggregation-inhibiting activity |
|---|---|
| (The compounds of the present invention) | |
| Ethyl 2-[2-(4-fluorophenyl)-5-(3-thienyl)-4-oxazolyl]-acetate | + |
| Ethyl 2-[2-(4-fluorophenyl)-5-(-2-thienyl)-4-oxazolyl]-acetate | + |
| 2-[2-(4-fluorophenyl)-5-(3-thienyl)-4-oxazolyl]-acetic acid | + |
| 2-[2-(4-fluorophenyl)-5-(2-thienyl)-4-oxazolyl]-acetic acid | + |
| 2-[2-(4-chlorophenyl)-5-(3-thienyl)-4-oxazolyl]-acetic acid | + |
| n-Pentyl 2-[2-phenyl-5-(3-thienyl)-4-oxazolyl]-acetate | + |
| (Positive control) | |
| Clofibrate | − |

Experiment 3

(Platelet aggregation-inhibiting activity)

A test compound was suspended in a 0.25% Tween 80 solution, and the suspension was administered orally to male SD rats (body weight: 200 to 240 g, a group of 4 rats). One hour after administration of the test compound (dose: 100 mg/kg), blood was collected from the abdominal aorta of the rats under ether anesthesia. Thereafter, said blood was treated in the same manner as described in Experiment 2, and the percentage inhibition of platelet aggregation was calculated in accordance with the following formula:

Percentage inhibition of platelet aggregation =

$$\left[1 - \frac{\text{Degree of platelet aggregation in the medicated group}}{\text{Degree of platelet aggregation in the control group}}\right] \times 100$$

(Results)
The results are shown in the following Table 3.

TABLE 3

| Test compound | Percentage inhibition of platelet aggregation |
|---|---|
| (The compound of the present invention) | |
| 2-[2-(4-fluorophenyl)-5-(3-thienyl)-4-oxazolyl]acetic acid | 93 ± 6 |

EXAMPLE 1

40 g of ethyl 3-(4-fluorobenzoylamino)-3-(3-thienylcarbonyl)propionate are dissolved in 150 ml of dimethylformamide, and 24.6 g of phosphorus oxychloride are added dropwise to the solution at 0° to 5° C. The mixture is stirred at the same temperature for 4 hours, and further stirred at room temperature overnight. After the reaction, the mixture is poured in water, and the aqueous mixture is neutralized with sodium bicarbonate and then extracted with ethyl acetate. The extract is washed with water, dried and then condensed under reduced pressure to remove solvent. The residue is recrystallized from ethanol, whereby 32.4 g of ethyl 2-[2-(4-fluorophenyl)-5-(3-thienyl)-4-oxazolyl]acetate are obtained.

Yield: 85.5%
M.p. 112°–113° C.
IR $\nu_{max}^{Nujol}$ (cm$^{-1}$): 1730

EXAMPLE 2

5.8 g of ethyl 3-benzoylamino-3-(3-thienylcarbonyl)-propionate, 30 ml of dimethylformamide and 3.8 g of phosphorus oxychloride are treated in the same manner as described in Example 1. 4.3 g of ethyl 2-[2-phenyl-5-(3-thienyl)-4-oxazolyl]acetate are thereby obtained.
Yield: 79%
M.p. 90°–91° C.
IR $\nu_{max}^{Nujol}$ (cm$^{-1}$): 1720, 1620

EXAMPLE 3

9.0 g of ethyl 3-(4-chlorobenzoylamino)-3-(3-thienylcarbonyl)propionate, 50 ml of dimethylformamide and 5.3 g of phosphorus oxychloride are treated in the same manner as described in Example 1. 6.7 g of ethyl 2-[2-(4-chlorophenyl)-5-(3-thienyl)-4-oxazolyl]acetate are thereby obtained.
Yield 78%
M.p. 127°–128° C.
IR $\nu_{max}^{Nujol}$ (cm$^{-1}$): 1730, 1630

EXAMPLE 4

13 g of methyl 3-(4-chlorobenzoylamino)-3-(3-thienylcarbonyl)propionate, 50 ml of dimethylformamide and 9.6 g of phosphorus oxychloride are treated in the same manner as described in Example 1. 11 g of methyl 2-[2-(4-chlorophenyl)-5-(3-thienyl)-4-oxazolyl]acetate are thereby obtained.
Yield: 89%
M.p. 127°–128° C.
IR $\nu_{max}^{Nujol}$ (cm$^{-1}$): 1740, 1623

EXAMPLE 5

1.5 g of ethyl 3-benzoylamino-3-(2-thienylcarbonyl)propionate, 10 ml of dimethylformamide and 0.5 g of phosphorus oxychloride are treated in the same manner as described in Example 1. 1.1 g of ethyl 2-[2-phenyl-5-(2-thienyl)-4-oxazolyl]acetate are thereby obtained.
Yield: 79%
M.p. 82°–83° C.
IR $\nu_{max}^{Nujol}$ (cm$^{-1}$): 1725, 1618

EXAMPLE 6

38.6 g of ethyl 3-(4-fluorobenzoylamino)-3-(2-thienylcarbonyl)propionate, 100 ml of dimethylformamide and 20.3 g of phosphorus oxychloride are treated in the same manner as described in Example 1. 27.4 g of ethyl 2-[2-(4-fluorophenyl)-5-(2-thienyl)-4-oxazolyl]acetate are thereby obtained.
Yield: 74%
M.p. 116°–117° C.
IR $\nu_{max}^{Nujol}$ (cm$^{-1}$): 1720, 1620

EXAMPLE 7

2.8 g of ethyl 3-(4-chlorobenzoylamino)-3-(2-thienylcarbonyl)propionate, 10 ml of dimethylformamide and 1.4 g of phosphorus oxychloride are treated in the same manner as described in Example 1. 2.2 g of ethyl 2-[2-(4-chlorophenyl)-5-(2-thienyl)-4-oxazolyl]acetate are thereby obtained.
Yield: 83%
M.p. 119°–120° C.
IR $\nu_{max}^{Nujol}$ (cm$^{-1}$): 1730, 1620

EXAMPLE 8

27.3 g of ethyl 2-[2-(4-fluorophenyl)-5-(3-thienyl)-4-oxazolyl]acetate are dissolved in a mixture of 700 ml of methanol and 100 ml of water, and 10.9 g of potassium hydroxide are added thereto. The mixture is stirred at room temperature for 17 hours. After the reaction, the mixture is condensed under reduced pressure to remove methanol. Water is added to the residue, and the aqueous mixture is adjusted to pH 2 with conc. hydrochloric acid. The mixture is extracted with ethyl acetate, and the extract is washed with water, dried and then condensed under reduced pressure to remove solvent. The residue is recrystallized from ethanol, whereby 22.3 g of 2-[2-(4-fluorophenyl)-5-(3-thienyl)-4-oxazolyl]acetic acid are obtained.
Yield: 89%
M.p. 207°–209° C.
IR $\nu_{max}^{Nujol}$ (cm$^{-1}$): 1720

EXAMPLE 9

14.0 g of ethyl 2-[2-(4-fluorophenyl)-5-(2-thienyl)-4-oxazolyl]acetate, 300 ml of methanol, 30 ml of water and 5.6 g of potassium hydroxide are treated in the same manner as described in Example 8. 11.7 g of 2-[2-(4-fluorophenyl)-5-(2-thienyl)-4-oxazolyl]acetic acid are thereby obtained.
Yield: 91.3%
M.p. 208°–209° C.
IR $\nu_{max}^{Nujol}$ (cm$^{-1}$): 1720

EXAMPLE 10

15.0 g of ethyl 2-[2-phenyl-5-(3-thienyl)-4-oxazolyl]acetate, 250 ml of methanol, 20 ml of water and 6.3 g of potassium hydroxide are treated in Example 8. 12.0 g of 2-[2-phenyl-5-(3-thienyl)-4-oxazolyl]acetic acid are thereby obtained. Yield: 88%
M.p. 186.5°–187.5° C.
IR $\nu_{max}^{Nujol}$ (cm$^{-1}$): 1725

EXAMPLE 11

(1) 6 g of ethyl 2-[2-(4-chlorophenyl)-5-(3-thienyl)-4-oxazolyl]acetate, 150 ml of methanol, 30 ml of water and 2.2 g of potassium hydroxide are treated in the same manner as described in Example 8. 4.9 g of 2-[2-(4-chlorophenyl)-5-(3-thienyl)-4-oxazolyl]acetic acid are thereby obtained.
Yield: 89%
M.p. 218°–219° C.
IR $\nu_{max}^{Nujol}$ (cm$^{-1}$): 1720

(2) 3.0 g of 2-[2-(4-chlorophenyl)-5-(3-thienyl)-4-oxazolyl]acetic acid are added to 20 ml of an aqueous 50% methanol solution containing sodium hydroxide (content: 0.4 g/20 ml), and the mixture is stirred at room temperature for 3 hours. After the reaction, the mixture is condensed under reduced pressure to remove solvent. The residue is washed with cold ethanol and ether, whereby 2.9 g of sodium 2-[2-(4-chlorophenyl)-5-(3-thienyl)-4-oxazolyl]acetate are obtained. Yield: 90%
M.p. >250° C.
IR $\nu_{max}^{Nujol}$ (cm$^{-1}$): 1593

EXAMPLE 12

2.7 g of ethyl 2-[2-(4-fluorophenyl)-5-(3-thienyl)-4-oxazolyl]acetate are dissolved in 10 ml of 10% potassium hydroxide/methanol, and the solution is stirred at room temperature for 17 hours. After the reaction, the crystalline precipitates are collected by filtration, and then washed with cold ethanol and ether. 2.4 g of potassium 2-[2-(4-fluorophenyl)-5-(3-thienyl)-4-oxazolyl]acetate are thereby obtained.
Yield: 80%
M.p. >250° C.
IR $\nu_{max}^{Nujol}$ (cm$^{-1}$): 1580

EXAMPLE 13

2 g of 2-[2-(4-chlorophenyl)-5-(3-thienyl)-4-oxazolyl]acetic acid are dissolved in 2 ml of toluene, and 3 g of thionyl chloride are added thereto. The mixture is stirred at room temperature overnight. After the reaction, the mixture is condensed under reduced pressure. 30 ml of n-pentanol are added to the residue, and the mixture is stirred at room temperature for 4 hours. Then, the mixture is condensed under reduced pressure to remove n-pentanol, and the residue is extracted with ethyl acetate. The extract is washed with an aqueous sodium bicarbonate solution and water, successively. Then, the extract is dried and then condensed under reduced pressure to remove solvent. The residue is recrystallized from ethanol, whereby 1.2 g of n-pentyl 2-[2-(4-chlorophenyl)-5-(3-thienyl)-4-oxazolyl]acetate are obtained. Yield: 49%

M.p. 86°–87° C.

IR $\nu_{max}^{Nujol}$ (cm$^{-1}$): 1730, 1625

EXAMPLE 14

2 g of 2-[2-phenyl-5-(3-thienyl)-4-oxazolyl]acetic acid, 3 g of thionyl chloride and 30 ml of isopropanol are treated in the same manner as described in Example 13. One g of isopropyl 2-[2-phenyl-5-(3-thienyl)-4-oxazolyl]acetate is obtained. Yield: 43%

M.p. 62°–63° C.

IR $\nu_{max}^{Nujol}$ (cm$^{-1}$): 1725, 1631

EXAMPLE 15

2 g of 2-[2-phenyl-5-(3-thienyl)-4-oxazolyl]acetic acid, 3 g of thionyl chloride and 30 ml of n-butanol are treated in the same manner as described in Example 13. 0.8 g of n-butyl 2-[2-phenyl-5-(3-thienyl)-4-oxazolyl]acetate is thereby obtained. Yield: 33.5%

M.p. 71°–72° C.

IR $\nu_{max}^{Nujol}$ (cm$^{-1}$): 1725, 1630

EXAMPLE 16

2 g of 2-[2-phenyl-5-(3-thienyl)-4-oxazolyl]acetic acid, 3 g of thionyl chloride and 30 ml of n-pentanol are treated in the same manner as described in Example 13. One g of n-pentyl 2-[2-phenyl-5-(3-thienyl)-4-oxazolyl]acetate is thereby obtained. Yield: 40.2%

M.p. 61°–62° C.

IR $\nu_{max}^{Nujol}$ (cm$^{-1}$): 1725, 1625

EXAMPLE 17

2.6 g of 2-[2-(4-chlorophenyl)-5-(3-thienyl)-4-oxazolyl]acetic acid are added to 20 ml of an aqueous 50% methanol solution containing potassium hydroxide (content: 0.54 g/20 ml), and the mixture is stirred at room temperature for 3 hours. Then, the mixture is condensed under reduced pressure to remove solvent. 6.4 g of oxalyl chloride are added to the residue, and the mixture is stirred overnight. Then, the mixture is condensed under reduced pressure to remove excess of oxalyl chloride. 20 ml of isopropanol are added to the residue, and the mixture is stirred at room temperature for 5 hours. After the reaction, the mixture is condensed under reduced pressure to remove solvent. The residue is extracted with ethyl acetate. The extract is washed with an aqueous sodium bicarbonate solution and water, successively. Then, the extract is dried and then condensed under reduced pressure to remove solvent. The residue is recrystallized from ethanol, whereby 1.6 g of isopropyl 2-[2-(4-chlorophenyl)-5-(3-thienyl)-4-oxazolyl]acetate are obtained.

Yield: 55%

M.p. 118°–119° C.

IR $\nu_{max}^{Nujol}$ (cm$^{-1}$): 1725, 1630

EXAMPLE 18

2 g of 2-[2-(4-fluorophenyl)-5-(3-thienyl)-4-oxazolyl]acetic acid, 0.5 g of potassium hydroxide, 4.2 g of oxalyl chloride and 20 ml of n-butanol are treated in the same manner as described in Example 17. One g of n-butyl 2-[2-(4-fluorophenyl)-5-(3-thienyl)-4-oxazolyl]acetate is thereby obtained. Yield: 42.2%

M.p. 81°–82° C.

IR $\nu_{max}^{Nujol}$ (cm$^{-1}$): 1730, 1630, 1610

EXAMPLE 19

2 g of 2-[2-(4-fluorophenyl)-5-(3-thienyl)-4-oxazolyl]acetic acid, 0.5 g of potassium hydroxide, 4.2 g of oxalyl chloride and 20 ml of n-pentanol are treated in the same manner as described in Example 17. 1.3 g of n-pentyl 2-[2-(4-fluorophenyl)-5-(3-thienyl)-4-oxazolyl]acetate are thereby obtained. Yield: 52.8%

M.p. 78°–80° C.

IR $\nu_{max}^{Nujol}$ (cm$^{-1}$): 1730, 1630, 1610

EXAMPLE 20

One g of 2-[2-(4-fluorophenyl)-5-(3-thienyl)-4-oxazolyl]acetic acid, 0.93 g of 2-chloro-1-methylpyridinium iodide and 0.2 g of isopropanol are dissolved in 40 ml of tetrahydrofuran, and 0.66 g of triethylamine is added dropwise thereto. The mixture is stirred at room temperature for 18 hours. Then, water is added to the reaction mixture, and said mixture is condensed under reduced pressure to remove tetrahydrofuran. The residue is extracted with ethyl acetate, and the extract is washed with an aqueous 20% citric acid solution, an aqueous sodium bicarbonate solution and water, successively. Said extract is dried and then condensed to remove solvent, and the residue is recrystallized from ethanol. 0.85 g of isopropyl 2-[2-(4-fluorophenyl)-5-(3-thienyl)-4-oxazolyl]acetate is thereby obtained.

Yield: 74.6%

M.p. 108°–110° C.

IR $\nu_{max}^{Nujol}$ (cm$^{-1}$): 1730, 1630, 1605

EXAMPLE 21

0.55 g of 2-[2-(4-chlorophenyl)-5-(3-thienyl)-4-oxazolyl]acetic acid, 0.44 g of 2-chloro-1-methylpyridinium iodide, 0.13 ml of n-butanol and 0.2 g of triethylamine are treated in the same manner as described in Example 20. 0.45 g of n-butyl 2-[2-(4-chlorophenyl)-5-(3-thienyl)-4-oxazolyl]acetate is thereby obtained.

Yield: 69.1%

M.p. 79°–81° C.

IR $\nu_{max}^{Nujol}$ (cm$^{-1}$): 1730, 1625

EXAMPLE 22

13 g of ethyl 3-(2-chlorobenzoylamino)-3-(3-thienylcarbonyl)propionate, 7.05 g of phosphorus oxychloride and 130 ml of dimethylformamide are treated in the same manner as described in Example 1. 8.2 g of ethyl 2-[2-(2-chlorophenyl)-5-(3-thienyl)-4-oxazoyl]acetate are thereby obtained.

Yield: 68.3%

M.p. 73°–75° C.

IR $\nu_{max}^{Nujol}$ (cm$^{-1}$): 1725, 1620

EXAMPLE 23

9.0 g of ethyl 3-(3-chlorobenzoylamino)-3-(3-thienylcarbonyl)propionate, 6.75 g of phosphorus oxychloride and 80 ml of dimethylformamide are treated in the same manner as described in Example 1. 6.4 g of ethyl 2-[2-(3-chlorophenyl)-5-(3-thienyl)-4-oxazoyl]acetate are thereby obtained.

Yield: 72.7%
M.p. 128°–130° C.
IR $\nu_{max}^{Nujol}$ (cm$^{-1}$): 3100 1730, 1630, 1600

EXAMPLE 24

3.5 g of ethyl 2-[2-(2-chlorophenyl)-5-(3-thienyl)-4-oxazolyl]acetate, 75 ml of methanol, 7.5 g of water and 1.4 g of potassium hydroxide are treated in the same manner as described in Example 8. 2.84 g of 2-[2-(2-chlorophenyl)-5-(3-thienyl)-4-oxazolyl]acetic acid are thereby obtained.

Yield: 89.1%
M.p. 163°–165° C.
IR $\nu_{max}^{Nujol}$ (cm$^{-1}$): 1728, 1630

EXAMPLE 25

3.5 g of ethyl 2-[2-(3-chlorophenyl)-5-(3-thienyl)-4-oxazolyl]acetate, 75 ml of methanol, 7.5 ml of water and 1.4 g of potassium hydroxide are treated in the same manner as described in Example 8. 2.96 g of 2-[2-(3-chlorophenyl-5-(3-thienyl)-4-oxazolyl]acetic acid are thereby obtained.

Yield: 92.6%
M.p. 194°–197° C.
IR $\nu_{max}^{Nujol}$ (cm$^{-1}$): 1710, 1630, 1600

Preparation 1

(1) 100 g of methyl α-isocyanoacetate and 400 g of triethylamine are dissolved in 2.5 liters of tetrahydrofuran, and 159 g of 3-thienylcarbonyl chloride are added dropwise thereto at room temperature under stirring. The mixture is further stirred at the same temperature for 48 hours. Then, the reaction mixture is condensed under reduced pressure to remove solvent. The residue is extracted with ethyl acetate, and the extract is washed with water and then with diluted hydrochloric acid. Said extract is dried and then condensed under reduced pressure to remove solvent. The residue is recrystallized from isopropyl ether, whereby 167 g of 5-(3-thienyl)-4-methoxycarbonyloxazole are obtained.

Yield: 80%
M.p. 62°–64° C. (recrystallized from a mixture of isopropyl ether and ethyl acetate)
IR $\nu_{max}^{Nujol}$ (cm$^{-1}$): 3140, 1700, 1592

(2) A mixture of 20.9 g of 5-(3-thienyl)-4-methoxycarbonyloxazole and 100 ml of 6N hydrochloric acid is stirred at 80° to 90° C. for 4 hours. Then, the reaction mixture is condensed under reduced pressure, and the residue is crystallized with acetone. 16.2 g of N-[(3-thienylcarbonyl)methyl]amine hydrochloride are thereby obtained.

Yield: 91%
M.p. 179°–180° C. (decomp.) (recrystallized from methanol)
IR $\nu_{max}^{Nujol}$ (cm$^{-1}$): 1685, 1580

(3) 16 g of 4-fluorobenzoyl chloride are dissolved in 50 ml of ethyl acetate, and the solution is added at a temperature below 10° C. under stirring to a mixture of 17.8 g of N-[(3-thienylcarbonyl)methyl]amine hydrochloride, 25 g of sodium bicarbonate, 100 ml of ethyl acetate and 200 ml of water. The mixture is further stirred at room temperature for 3 hours. The precipitated crystals are collected by filtration, washed with water and then dried, whereby N-(4-fluorobenzoyl)-N-[(3-thienylcarbonyl)methyl]amine is obtained. On the other hand, the filtrate is washed with water, dried and then condensed under reduced pressure to remove solvent. The residue is washed with ether, whereby N-(4-fluorobenzoyl)-N-[(3-thienylcarbonyl)methyl]amine is further obtained.

Total amount: 25.5 g
Yield: 25.5%
M.p. 140°–141° C. (recrystallized from methanol)
IR $\nu_{max}^{Nujol}$ (cm$^{-1}$): 3340, 1680, 1630, 1600

(4) 65.0 g of N-(4-fluorobenzoyl)-N-[(3-thienylcarbonyl)methyl]amine are dissolved in 350 ml of dimethylformamide. 14.2 g of 50% sodium hydride are added to the solution at −40° to −50° C. under stirring, and the mixture is further stirred at the same temperature for 5 minutes. 45.3 g of ethyl bromoacetate are added to the mixture, and said mixture is stirred at 0° C. for one hour. After the reaction, the mixture is neutralized with acetic acid, and water is added thereto. The aqueous mixture is extracted with ethyl acetate, and the extract is washed with an aqueous sodium bicarbonate solution and then with water. Said extract is dried and then condensed under reduced pressure to remove solvent. The residue is recrystallized from a mixture of ethanol and isopropyl ether, whereby 57.0 g of ethyl 3-(4-fluorobenzoylamino)-3-(3-thienylcarbonyl)propionate are obtained. Yield: 66%

M.p. 75°–77° C.
IR $\nu_{max}^{Nujol}$ (cm$^{-1}$): 3350, 1730, 1660

Preparation 2

(1) 29.7 g of methyl α-isocyanoacetate, 120 g of triethylamine, 450 ml of tetrahydrofuran and 48.4 g of 2-thienylcarbonyl chloride are treated in the same manner as described in Preparation 1-(1). 53.9 g of 5-(2-thienyl)-4-methoxycarbonyloxazole are thereby obtained.

Yield: 86%
M.p. 64°–66° C. (recrystallized from isopropyl ether)
IR $\nu_{max}^{Nujol}$ (cm$^{-1}$): 3130, 1700, 1596

(2) 53.9 g of 5-(2-thienyl)-4-methoxycarbonyloxazole and 200 ml of 6N hydrochloric acid are treated in the same manner as described in Preparation 1-(2). 42.5 g of N-[(2-thienylcarbonyl)methyl]amine hydrochloride are thereby obtained. Yield: 93%

M.p. 213°–214° C. (decomp.) (recrystallized from ethanol)
IR $\nu_{max}^{Nujol}$ (cm$^{-1}$): 1670, 1570

(3) 5 g of N-[(2-thienylcarbonyl)methyl]amine hydrochloride, 10 g of sodium bicarbonate and 3.9 g of benzoyl chloride are treated in the same manner as described in Preparation 1-(3). 6.4 g of N-benzoyl-N-[(2-thienylcarbonyl)methyl]amine are thereby obtained. Yield: 93.3%

M.p. 146°–147° C. (recrystallized from ethyl acetate)
IR $\nu_{max}^{Nujol}$ (cm$^{-1}$): 3420, 1660, 1600

(4) 4.0 g of N-benzoyl-N-[(2-thienylcarbonyl)methyl]amine, one g of 50% sodium hydride and 2.7 g of ethyl bromoacetate are treated in the same manner as described in Preparation 1-(4). 3.4 g of ethyl 3-benzoylamino-3-(2-thienylcarbonyl)propionate are obtained.

Yield: 63%
M.p. 75°–75° C.

IR $\nu_{max}^{Nujol}$ (cm$^{-1}$): 3280, 1735, 1725, 1655, 1635

Preparation 3

(1) 4 g of N-[(3-thienylcarbonyl)methyl]amine hydrochloride, 8 g of sodium bicarbonate and 3.6 g of benzoyl chloride are treated in the same manner as described in Preparation 1-(3). 5.25 g of N-benzoyl-N-[(3-thienylcarbonyl)methyl]amine are thereby obtained.
Yield: 95%
M.p. 118°–119° C. (recrystallized from ethyl acetate)
IR $\nu_{max}^{Nujol}$ (cm$^{-1}$): 3300, 3080, 1690, 1630, 1600

(2) 4.7 g of N-benzoyl-N-[(3-thienylcarbonyl)methyl]amine, 1.1 g of 50% sodium hydride and 3.9 g of ethyl bromoacetate are treated in the same manner as described in Preparation 1-(4). 4.2 g of ethyl 3-benzoylamino-3-(3-thienylcarbonyl)propionate are thereby obtained.
Yield: 68%
M.p. 62°–63° C.
IR $\nu_{max}^{Nujol}$ (cm$^{-1}$): 3320, 1740, 1730, 1685, 1640

Preparation 4

(1) 19.4 g of N-[(3-thienylcarbonyl)methyl]amine hydrochloride, 36 g of sodium bicarbonate and 21 g of 4-chlorobenzoyl chloride are treated in the same manner as described in Preparation 1-(3). 29 g of N-(4-chlorobenzoyl)-N-[(3-thienylcarbonyl)methyl]amine are thereby obtained.
M.p. 160°–161° C. (recrystallized from ethyl acetate)
IR $\nu_{max}^{Nujol}$ (cm$^{-1}$): 3350, 1680, 1635, 1595

(2) 15.0 g of N-(4-chlorobenzoyl)-N-[(3-thienylcarbonyl)methyl]amine, 3.1 g of 50% sodium hydride and 10 g of ethyl bromoacetate are treated in the same manner as described in Preparation 1-(4). 14.1 g of ethyl 3-(4-chlorobenzoylamino)-3-(3-thienylcarbonyl)propionate are thereby obtained. Yield: 71.4%
M.p. 106°–108° C.
IR $\nu_{max}^{Nujol}$ (cm$^{-1}$): 3300, 1735, 1685, 1630

Preparation 5

(1) 20.8 g of N-[(2-thienylcarbonyl)methyl]amine hydrochloride, 40.0 g of sodium bicarbonate and 18.5 g of 4-fluorobenzoyl chloride are treated in the same manner as described in Preparation 1-(3). 29 g of N-(4-fluorobenzoyl)-N-[(2-thienylcarbonyl)methyl]amine are thereby obtained.
Yield: 94%
M.p. 147°–148° C. (recrystallized from ethyl acetate)
IR $\nu_{max}^{Nujol}$ (cm$^{-1}$): 3400, 3100, 1665, 1650, 1600

(2) 31.6 g of N-(4-fluorobenzoyl)-N-[(2-thienylcarbonyl)methyl]amine, 6.9 g of 50% sodium hydride and 20 g of ethyl bromoacetate are treated in the same manner as described in Preparation 1-(4). 37.7 g of 3-(4-fluorobenzoylamino)-3-(2-thienylcarbonyl)propionate are thereby obtained as an oil. Yield: 90%
IR $\nu_{max}^{film}$ (cm$^{-1}$): 3300, 1740, 1730, 1660

Preparation 6

(1) 5.0 g of N-[(2-thienylcarbonyl)methyl]amine hydrochloride, 10.0 g of sodium bicarbonate and 4.78 g of 4-chlorobenzoyl chloride are treated in the same manner as described in Preparation 1-(3). 7.6 g of N-(4-chlorobenzoyl)-N-[(2-thienylcarbonyl)methyl]amine are thereby obtained.
Yield: 97%
M.p. 157°–159° C. (recrystallized from ethyl acetate)
IR $\nu_{max}^{Nujol}$ (cm$^{-1}$): 3320, 3100, 1670, 1640, 1595

(2) 5 g of N-(4-chlorobenzoyl)-N-[(2-thienylcarbonyl)methyl]amine, 1.03 g of 50% sodium hydride and 2.98 g of ethyl bromoacetate are treated in the same manner as described in Preparation 1-(4). 4.3 g of ethyl 3-(4-chlorobenzoylamino)-3-(2-thienylcarbonyl)propionate are thereby obtained.
Yield: 65.7%
M.p. 112°–113° C.
IR $\nu_{max}^{Nujol}$ (cm$^{-1}$): 3320, 1740, 1730, 1660, 1630

Preparation 7

23 g of N-(4-chlorobenzoyl)-N-[(3-thienylcarbonyl)methyl]amine, 6.1 g of 50% sodium hydride and 21.8 g of methyl bromoacetate are treated in the same manner as described in Preparation 1-(4). 18.6 g of methyl 3-(4-chlorobenzoylamino)-3-(3-thienylcarbonyl)propionate are thereby obtained.
Yield: 62%
M.p. 146°–148° C.
IR $\nu_{max}^{Nujol}$ (cm$^{-1}$): 3280, 1745, 1680, 1623

Preparation 8

(1) 7.5 g of N-[(3-thienylcarbonyl)methyl]amine hydrochloride, 10.0 g of sodium bicarbonate and 8.86 g of 2-chlorobenzoyl chloride are treated in the same manner as described in Preparation 1-(3). 11.3 g of N-(2-chlorobenzoyl)-N-[(3-thienylcarbonyl)methyl]amine are thereby obtained.
Yield: 95.8%
M.p. 111°–112° C.
IR $\nu_{max}^{Nujol}$ (cm$^{-1}$): 3250, 3150, 3200, 1685, 1640, 1595

(2) 11.0 g of N-(2-chlorobenzoyl)-N-[(3-thienylcarbonyl)methyl]amine, 2.17 g of 50% sodium hydride and 7.9 g of ethyl bromoacetate are treated in the same manner as described in Preparation 1-(4). 14 g of ethyl 3-(2-chlorobenzoylamino)-3-(3-thienylcarbonyl)propionate are thereby obtained as an oil. Yield: 97.2%
IR $\nu_{max}^{film}$ (cm$^{-1}$): 3300, 3100, 1730, 1645

Preparation 9

(1) 7.5 g of N-[(3-thienylcarbonyl)methyl]amine hydrochloride, 10.0 g of sodium bicarbonate and 8.86 g of 3-chlorobenzoyl chloride are treated in the same manner as described in Preparation 1-(3). 11.0 g of N-(3-chlorobenzoyl)-N-[(3-thienylcarbonyl)methyl]amine are thereby obtained.
Yield: 93%
M.p. 137°–140° C.
IR $\nu_{max}^{Nujol}$ (cm$^{-1}$): 3300, 3100, 1700, 1645

(2) 11.0 g of N-(3-chlorobenzoyl)-N-[(3-thienylcarbonyl)methyl]amine, 2.17 g of 50% sodium hydride and 7.9 g of ethyl bromoacetate are treated in the same manner as described in Preparation 1-(4). 9.0 g of ethyl 3-(3-chlorobenzoylamino)-3-(3-thienylcarbonyl)propionate are thereby obtained. Yield: 62.5%
M.p. 63°–65° C.
IR $\nu_{max}^{KBr}$ (cm$^{-1}$): 3250, 1730, 1680, 1640, 1600

What we claim is:

1. A compound of the formula:

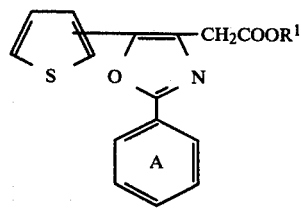

wherein Ring A is phenyl or halogenophenyl and $R^1$ is hydrogen or lower alkyl.

2. The compound of claim 1, in which Ring A is phenyl, fluorophenyl or chlorophenyl.

3. The compound of claim 1, in which Ring A is phenyl, 4-fluorophenyl, 2-chlorophenyl, 3-chlorophenyl or 4-chlorophenyl.

4. The compound of claim 1, in which Ring A is phenyl, 4-fluorophenyl or 4-chlorophenyl.

5. The compound of either one of claims 1 through 4, in which $R^1$ is hydrogen.

6. A pharmaceutically acceptable salt of the compound claimed in claim 5.

7. The compound of either one of claims 1 through 4, in which $R^1$ is lower alkyl.

8. The compound of claim 1, in which Ring A is phenyl, 4-fluorophenyl, 2-chlorophenyl, 3-chlorophenyl or 4-chlorophenyl, and $R^1$ is hydrogen, methyl, ethyl, isopropyl, n-butyl or n-pentyl.

9. The compound of claim 1, in which Ring A is phenyl, 4-fluorophenyl or 4-chlorophenyl, and $R^1$ is hydrogen, ethyl, n-butyl or n-pentyl.

10. The compound of claim 1, in which Ring A is phenyl, 4-fluorophenyl or 4-chlorophenyl, and $R^1$ is hydrogen, ethyl or n-pentyl.

11. The compound of claim 1, in which Ring A is phenyl or 4-fluorophenyl, and $R^1$ is ethyl or n-pentyl.

12. The compound of claim 11, which is ethyl 2-[2-(4-fluorophenyl)-5-(3-thienyl)-4-oxazolyl]acetate.

13. The compound of claim 11, which is ethyl 2-[2-(4-fluorophenyl)-5-(2-thienyl)-4-oxazolyl]acetate.

14. The compound of claim 11, which is n-pentyl 2-[2-phenyl-5-(3-thienyl)-4-oxazolyl]acetate.

15. The compound of claim 10 which is 2-[2-(4-fluorophenyl)-5-(3-thienyl)-4-oxazolyl]acetic acid.

16. A pharmaceutical composition for treating hyperlipidemia or platelet aggregation comprising a therapeutically effective amount of a compound of the formula:

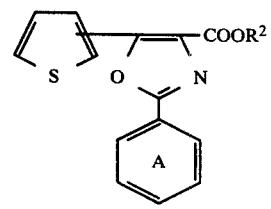

wherein Ring A is phenyl or halogenophenyl and $R^2$ is lower alkyl, and a pharmaceutically acceptable carrier therefor.

17. A pharmaceutical composition for treating hyperlipidemia or platelet aggregation comprising a therapeutically effective amount of a compound of the formula:

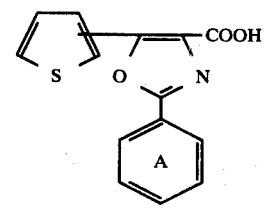

wherein Ring A is phenyl or halogenophenyl, or a pharmaceutically acceptable salt thereof, and a pharmaceutically acceptable carrier therefor.

* * * * *